(12) United States Patent
Gulliver et al.

(10) Patent No.: US 10,933,210 B2
(45) Date of Patent: Mar. 2, 2021

(54) NASAL CANNULA WITH TURBULATION ELEMENTS

(71) Applicant: Fisher & Paykel Healthcare Limited, Auckland (NZ)

(72) Inventors: Laurence Gulliver, Auckland (NZ); Mark Thomas O'Connor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 535 days.

(21) Appl. No.: 15/022,451

(22) PCT Filed: Sep. 19, 2014

(86) PCT No.: PCT/NZ2014/000205
§ 371 (c)(1),
(2) Date: Mar. 16, 2016

(87) PCT Pub. No.: WO2015/041547
PCT Pub. Date: Mar. 26, 2015

(65) Prior Publication Data
US 2016/0220775 A1 Aug. 4, 2016

Related U.S. Application Data

(60) Provisional application No. 61/881,321, filed on Sep. 23, 2013.

(51) Int. Cl.
*A61M 16/06* (2006.01)

(52) U.S. Cl.
CPC ...... *A61M 16/0666* (2013.01); *A61M 2206/11* (2013.01); *A61M 2206/14* (2013.01); *A61M 2206/20* (2013.01)

(58) Field of Classification Search
CPC .............. A61M 16/00; A61M 16/0672; A61M 16/0666; A61M 16/0461; A61M 16/04;
(Continued)

(56) References Cited

U.S. PATENT DOCUMENTS 3,643,660 A   2/1972  Hudson et al.
4,034,499 A *  7/1977  Wild .................. A63H 5/00
                                                446/215
(Continued)

FOREIGN PATENT DOCUMENTS

GB          2465689        3/2011
WO   WO2005/079726 A1     9/2005
WO   WO2008/014543 A1     2/2008

OTHER PUBLICATIONS

International Search Report; PCT/NZ2014/000205; dated Dec. 22, 2014; 4 pages.

*Primary Examiner* — Justine R Yu
*Assistant Examiner* — Matthew D Ziegler
(74) *Attorney, Agent, or Firm* — Knobbe, Martens, Olson & Bear, LLP

(57) ABSTRACT

Nasal cannulas for providing respiratory therapy to patients can have a curved prong section that has turbulation elements on the inside curve of the prong. A flow of breathing gas moving through the prong may incur less resistance and create less noise when flowing through such a prong due to the promotion of favorable flow dynamics.

16 Claims, 3 Drawing Sheets

(58) Field of Classification Search
CPC .......... A61M 16/0465; A61M 2206/14; A61M 2206/10; A61M 2206/11; A61M 2206/20; A61M 25/02; A61M 25/00; A61M 25/0021; A61M 25/0043; A61M 39/00; A61M 39/08
See application file for complete search history.

(56) References Cited

U.S. PATENT DOCUMENTS

| | | | | |
|---|---|---|---|---|
| 4,621,953 | A * | 11/1986 | McGuth | F16L 57/06 138/39 |
| 6,019,753 | A * | 2/2000 | Pagan | A61M 16/04 604/523 |
| 7,493,902 | B2 | 2/2009 | White et al. | |
| 8,110,267 | B2 * | 2/2012 | Houston | A61F 2/06 138/118 |
| 8,136,527 | B2 * | 3/2012 | Wondka | A61M 16/06 128/200.24 |
| 8,225,796 | B2 * | 7/2012 | Davenport | A61B 5/087 128/204.18 |
| 2008/0172121 | A1 * | 7/2008 | Scholz | A61F 2/06 623/1.13 |
| 2009/0044808 | A1 * | 2/2009 | Guney | A61M 16/0666 128/206.24 |
| 2009/0045006 | A1 * | 2/2009 | Kondo | F01N 1/04 181/252 |
| 2009/0183739 | A1 * | 7/2009 | Wondka | A61M 16/06 128/207.18 |
| 2011/0232649 | A1 | 9/2011 | Collazo et al. | |
| 2015/0165151 | A1 * | 6/2015 | Payton | A61M 16/0672 128/205.25 |

\* cited by examiner

NASAL CANNULA WITH TURBULATION ELEMENTS

INCORPORATION BY REFERENCE TO ANY PRIORITY APPLICATIONS

This application claims the priority benefit of U.S. Provisional Application No. 61/881,321, titled "NASAL CANNULA WITH TURBULATION ELEMENTS", filed Sep. 23, 2013. Any and all applications for which a foreign or domestic priority claim is identified in the Application Data Sheet as filed with the present application are hereby incorporated by reference under 37 CFR 1.57.

TECHNICAL FIELD OF THE INVENTION

The present disclosure generally relates to systems and devices for providing gases to patients for respiratory therapy. More particularly, the present disclosure relates to nasal cannula interfaces for providing gases to patients via the nasal passages.

BACKGROUND OF THE INVENTION

Medical professionals may wish to provide patients with respiratory assistance in the form of supplemental oxygen or airflow for many reasons in ICU, other hospital, or home environments. Different types of interfaces for supplying gases to patients are available. For example, various nasal masks, full face masks, oral interfaces, nasal pillows, and nasal cannula interfaces exist. Nasal cannula interfaces may include two nasal prongs that are placed in the patient's nostrils to deliver gases to the patient.

SUMMARY OF THE INVENTION

A nasal cannula system typically comprises a cannula body defining a cavity, one or two prongs extending from the body, and gases supply tubing that extends from one or two sides of the body. In some prior art configurations, the prong may be curved rather than straight to better match the profile of the nares. However, as flow moves through a curved prong, the flow may develop turbulent eddies that may generate noise and increase resistance to flow. Thus, it is an object of the disclosure to provide patients with a nasal cannula that might be easier to use, or at least provide the public with a useful choice.

In some configurations, a nasal cannula comprises a cannula body defining a cavity and at least one curved nasal prong extending from the cannula. The prong has an interior passage in communication with the cavity. A turbulation element is on an inside curve of the prong.

In some configurations, the turbulation element is adapted to induce turbulence in a flow of breathing gas through the interior passage in a boundary layer at the inside curve.

In some configurations, the turbulation element extends along an entire length of a curved section of the prong.

In some configurations, the turbulation element extends along an entire circumferential length of the inside curve.

In some configurations, the turbulation element extends beyond the inside curve in a circumferential direction.

In some configurations, the turbulation element comprises a surface portion having a component that extends in a circumferential direction.

In some configurations, an initial portion of the prong extending from a portion of the cannula body defining the cavity is generally straight.

In some configurations, the turbulation element comprises a plurality of one or more of recesses, ridges, pits, protrusions, bumps, lumps or humps.

In some configurations, the turbulation element comprises random surface texturing.

In some configurations, features defining the turbulation element are elongated in a circumferential direction.

In some configurations, an average amplitude of features defining the turbulation element is between 0% and 5% of a diameter of the prong.

In some configurations, the prong is formed as a unitary structure with the cannula body.

In some configurations, the prong is formed separately from a portion of the cannula body that defines the cavity.

In some configurations, a nasal cannula system comprises a flow circuit defined by one or more of a source of breathing gas, a supply conduit and a cannula having at least one curved nasal prong. The flow circuit comprises a curved portion. At least one turbulation element is provided on an inside curve surface of the curved portion.

BRIEF DESCRIPTION OF THE DRAWINGS

Specific embodiments and modifications thereof will become apparent to those skilled in the art from the detailed description herein having reference to the figures that follow.

DETAILED DESCRIPTION

Figure 1:
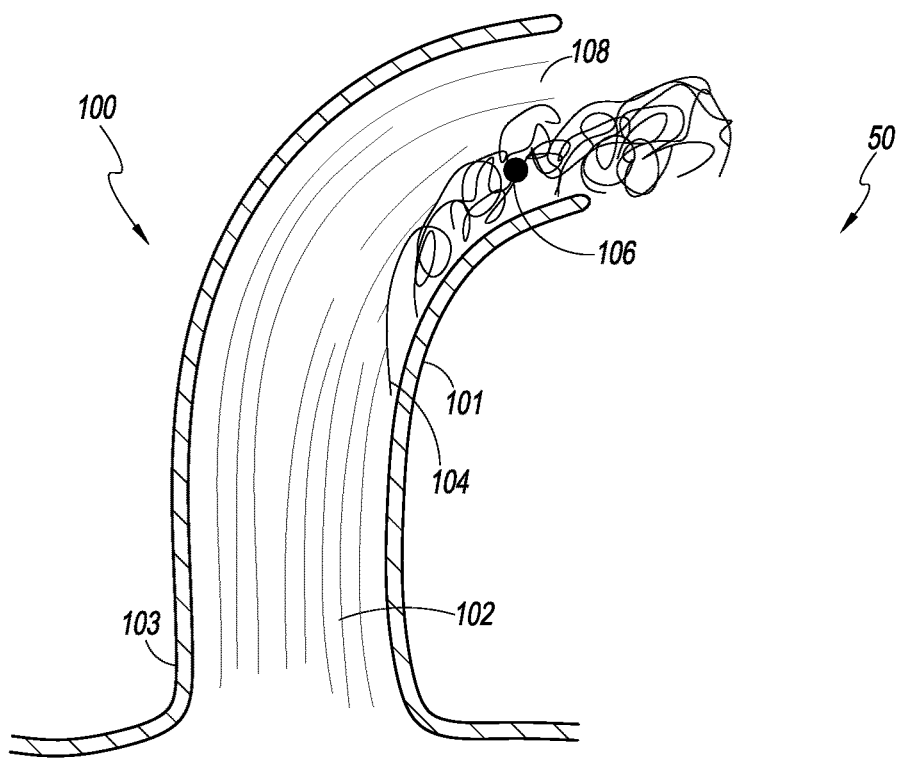
FIG. 1 is a side cross-sectional view of a nasal prong of a nasal cannula.

With reference to FIG. 1, a curved nasal cannula prong 100 with an initially laminar gas flow 102 moving through the prong 100 is shown. As laminar flow 102 passes through the relatively straight base 103 of the prong and into the more curved region 101, certain phenomena related to flow dynamics of the system can be observed. In this case, the flow may come to have a relatively low pressure on the inside of the curve and a relatively high pressure on the outside of the curve. In the low pressure area on the inside of the curve, the laminar flow in the boundary layer may be prone to flow separation at some point 104 along the flow path, which can separate the flow into a turbulent flow layer 106 and a laminar flow layer 108. An undesirable level of flow resistance and noise can arise from excessive turbulent flow like that present in the turbulent flow layer 106.

One way of mitigating the effects of the turbulent flow layer 106 is to place a turbulation element 110 on the surface of the inside curve of the prong 100. The turbulation element 110 may be or comprise one or a plurality of, for example, a pit, protrusion, recess, ridge, bump, lump, hump, and/or other element that may create a suitable surface roughness on the inside curve of the prong 100.

Figure 2:
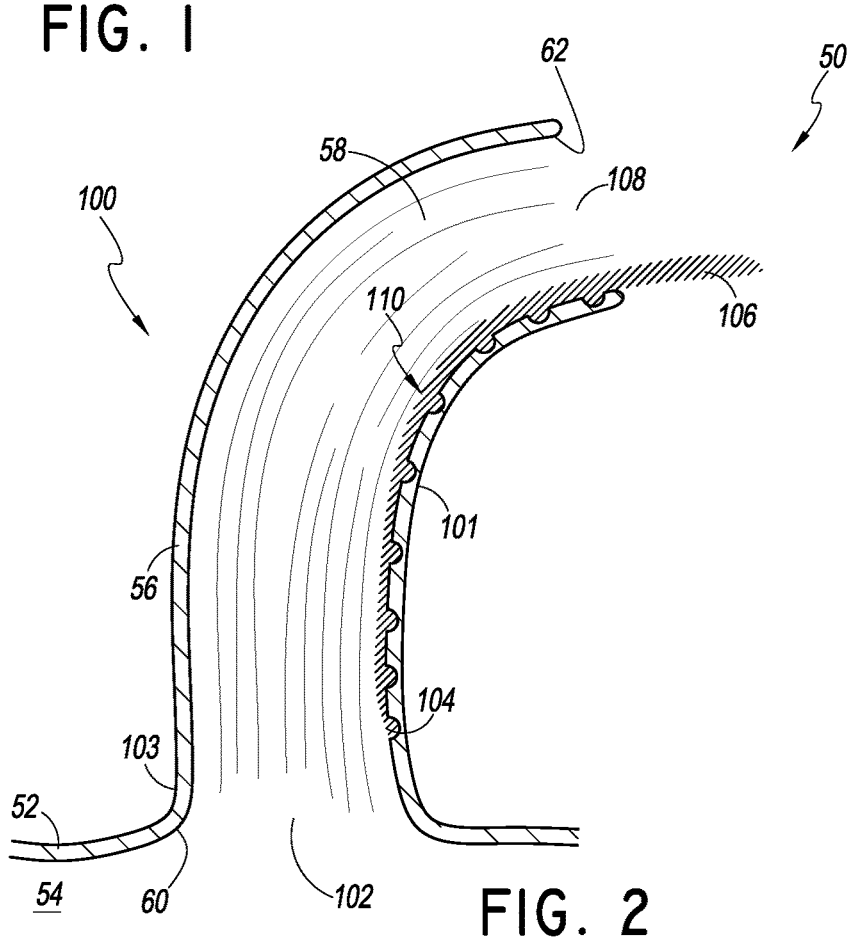
FIG. 2 is a side cross-sectional view of a nasal prong of a nasal cannula, wherein the prong comprises turbulation elements on the inside curve of the tube wall.

With reference to FIG. 2, a nasal cannula system 50 includes a cannula body 52 defining a cavity 54. The cannula body 52 can be held in place on the face of a user by any suitable arrangement, such as a headgear assembly or adhesive, for example. The cannula body 52 can be any size or shape suitable for being positioned on the face of the user and supporting one or two nasal prongs 100 for placement in the nares of the user. Similarly, the cavity 54 can be of any suitable size or shape for supplying a flow of breathing gas to the prongs 100. The flow of breathing gas can be provided by a gases source or generated by a blower, for example, and supplied to the cavity 54 by a suitable conduit, such as a breathing gas supply tube. In some embodiments, the prong 100 is a non-sealing nasal prong.

Each of the prongs 100 comprises a side wall 56 that defines an interior passage 58, which communicates with the cavity 54 to deliver the flow of breathing gas from the cavity 54 to the user's nares. The side wall 56 of the prongs 100 can be formed as a unitary structure with the cannula body 52 or can be formed separately, such as by a prong insert. The prongs 100 each have an opening at a first end, which is referred to as an inlet 60, and an opening at a second end, which is referred to as an outlet 62. The inlet 60 allows the flow of breathing gas to enter the passage 58 of the prong 100 from the cavity 54. The outlet 62 allows the flow of breathing gas to exit to passage 58 and the cannula system 50. Preferably, the side wall 56 comprises a curved portion such that the axes of the inlet 60 and outlet 62 or planes in which the inlet 60 and outlet 62 lie are non-parallel or angled relative to one another. The curved portion of the side wall 56 can define an inside curve or inside portion that is closest to the radius of the curve and an outside portion that is furthest from the radius of the curve. The curved portion can comprise a portion or an entirety of the side wall 56. In some configurations, an initial portion of the prong 100 extending from the cannula body 52 is generally straight or linear and a subsequent portion of the prong 100 is curved. Other features of the cannula system 50 can be similar to any of those disclosed in Applicant's application no. PCT/NZ2014/000040, filed Mar. 14, 2014, entitled NASAL CANNULA ASSEMBLIES AND RELATED PARTS, the entirety of which is incorporated by reference herein.

In the illustrated configuration of FIG. 2, one possible arrangement of a turbulation element 110 comprises at least one and preferably a plurality of depressions/recesses or ridges defined between the depressions. The depressions or ridges are provided along a length of the inside of the curve of the prong 100. The depressions or ridges can be provided along a portion of the length of the curve of the prong 100 or along a substantial entirety or an entirety of the length of the curve of the prong 100. In some configurations, the depressions or ridges are provided along a substantial entirety or an entirety of the length of the prong 100.

The depressions or ridges can be provided on only a portion of the inside portion of the curve of the prong 100 in a circumferential direction or direction around a longitudinal axis of the passage 58 or side wall 56 of the prong 100. In other arrangements, the depressions or ridges can be provided on an entirety of the inside portion of the curve of the prong 100. In some arrangements, it may be desirable or at least not harmful to the performance of the cannula system 50 to provide depressions or ridges on both inside portions and outside portions of the curve of the prong 100. Thus, in some arrangements, an entire interior surface of the side wall 56 of the prong 100 can comprise depressions or ridges. In some configurations, it may be desirable to provide depressions or ridges only on an outside portion of the curve or to omit the depressions or ridges on an inside portion of the curve while providing depressions or ridges elsewhere.

The depressions or ridges of the turbulation element 110 can be of any number, size or shape suitable to induce a desirable or effective level of laminar flow in the prong 100 or to provide a desirable or effective reduction in eddy currents, such as by inducing a turbulent boundary layer at the inside curve. The depressions or ridges can be elongated and can extend in a circumferential direction (or around the longitudinal axis) of the passage 58 of the prong 100 or can be offset from a circumferential direction or a direction perpendicular to the longitudinal axis of the passage 58. The depressions or ridges can be of a relatively short length, including round or square, and can be provided in a repeated pattern in a circumferential direction or a direction perpendicular to the longitudinal axis of the passage 58, Preferably, the depressions or ridges have at least a surface portion having a component that extends in a circumferential direction or a direction perpendicular to the longitudinal axis of the passage 58.

The size of the turbulation element 110 (e.g., a depth of the depressions or a height of the ridges) can be related to or selected based on characteristics or dimensions of the passage 58 of the prong 100, such as a particular proportion of the cross-sectional width or diameter, the cross-sectional area, the length or the radius of curvature of the passage 58, for example. The size of the turbulation element 110 can be related to or selected based on the flow characteristics of the flow of breathing gas through the passage 58 of the prong 100. The turbulation element 110 can be sized based on a combination of these factors or in view of other relevant factors, such as manufacturability or material considerations, for example, or any combination thereof.

In some configurations, as incoming flow 102 moves through the prong 100, the turbulation element 110 induces turbulence in a thin section of the boundary layer on the inside curve of the prong 100 at and/or around the point 104 where the flow encounters or runs along the element 110. The thin turbulent flow layer 106 created is much less prone to separation from the inside curve of the prong 100 than laminar flow, and so a larger portion of the flow may remain laminar and/or eddy currents are reduced relative to a prong 100 that does not comprise a turbulation element 110, which may decrease the flow resistance and noise of flow moving through the prong 100 in use.

Figure 3:
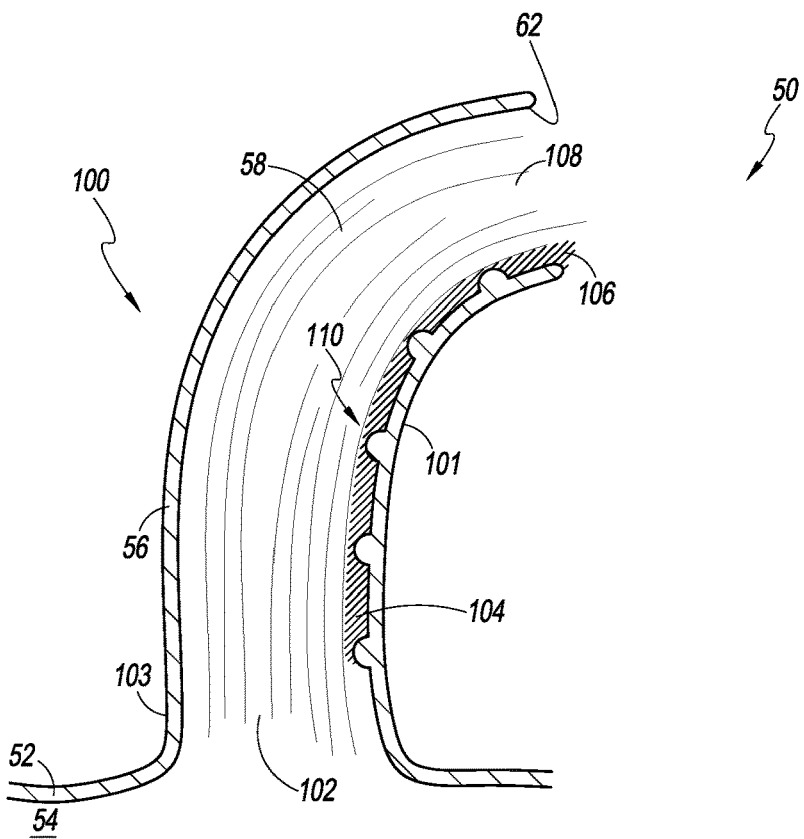
FIG. 3 is a side cross-sectional view of a nasal prong of a nasal cannula, wherein the prong comprises an alternative version of the turbulation elements on the inside curve of the tube wall.
Figure 4:
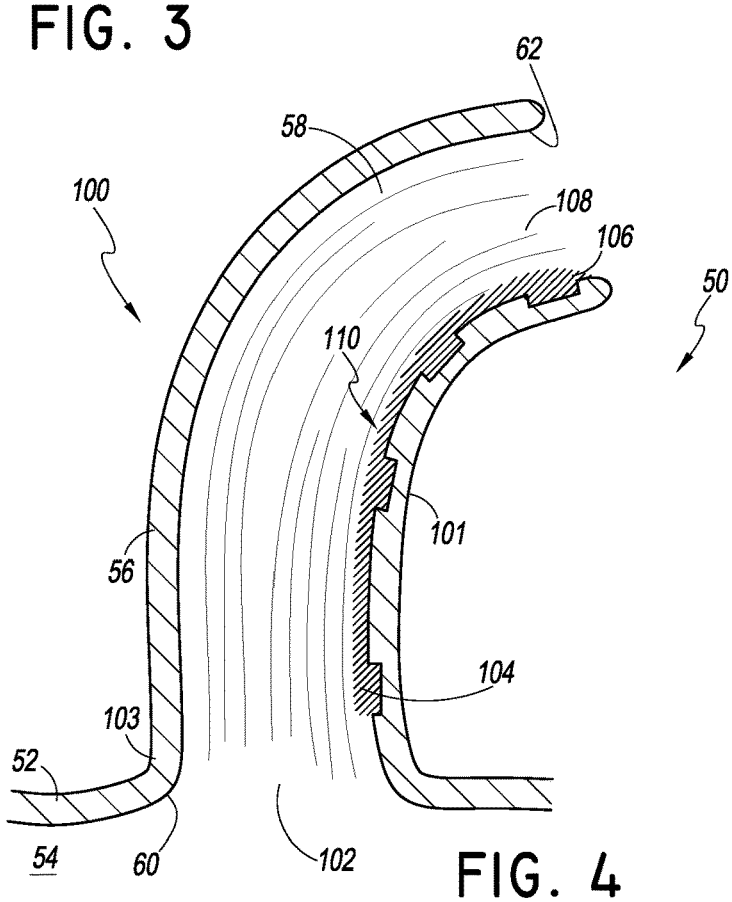
FIG. 4 is a side cross-sectional view of a nasal prong of a nasal cannula, where the prong comprises yet another alternative version of the turbulation elements on the inside curve of the tube wall.

There are no particular limitations as to the size, shape, number or arrangement of the individual features defining the turbulation element 110. Some possible configurations of the turbulation elements 110 are shown in FIGS. 3 and 4. Features or characteristics of such turbulation elements 110 or of the cannula systems in general can be the same as or similar to those described elsewhere herein or can be of any other suitable arrangement.

With reference to FIG. 3, the turbulation element 110 comprises at least one and preferably a plurality of raised bumps. The raised bumps can be, for example, a portion of a sphere, ovoid, cube, cuboid, cone, cylinder or other geometric shape. The number, size, shape and other characteristics can be selected as desired or as described herein.

With reference to FIG. 4, the turbulation element 110 comprises at least one and preferably a plurality of ridges and recesses. The ridges or recesses can be, for example, a portion of a sphere, ovoid, cube, cuboid, cone, cylinder or other geometric shape. The number, size, shape and other characteristics can be selected as desired or as described herein.

Figure 5:
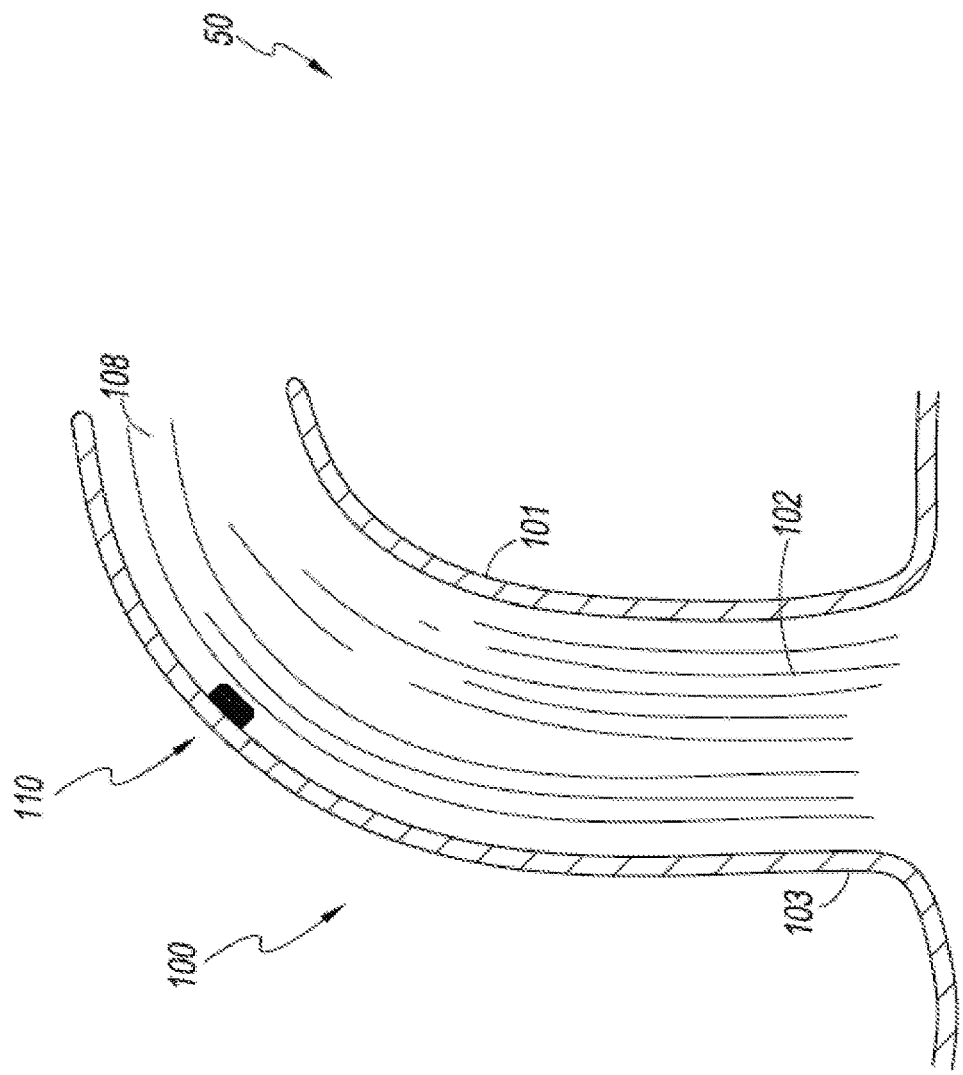
FIG. 5 is a side cross-sectional view of a nasal prong of a nasal cannula, wherein the prong comprises turbulation elements on the outside curve of the tube wall.

With reference to FIG. 5, the depressions or ridges can be provided on only on an outside onion of the curve. The turbulation element 110 is illustrated schematically. The curved onion of the side wall 56 can define an inside curve or inside portion that is closest to the radius of the curve and an outside curve or outside portion that is furthest from the radius of the curve.

In some configurations, the turbulation element 110 may comprise an ordered or random surface texture/roughness along a portion or an entirety of the inside curve of the prong 100. In a preferred configuration, the average amplitude of the surface roughness $R_a$ of the turbulation element 110 is between about 0% and 5% of the diameter (or other cross-sectional dimension) of the prong 100. In some configurations, the turbulation element 110 may instead be any feature that promotes a thin turbulent boundary layer on the inside curve of the prong 100. In some configurations, the element 110 is integrally formed with the cannula prong 100. In some configurations, the element 110 is a component separate from the cannula prong 100. In some configurations, the element 110 may be placed on any inside curve of the prong 100. In some configurations, the element 110 may circumscribe the internal walls of the prong 100. Additionally, such turbulation elements 110 may be beneficially placed anywhere in which there is a curved section in the flow path of the cannula circuit, e.g., prongs, curved parts of the gases supply tube, within the flow generator/flow source, in the gases flow manifold/prong transition, et cetera.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of an embodiment of the present invention have been described with reference to nasal cannulas. However, certain features, aspects and advantages of the nasal cannulas as described above may be advantageously used with other therapeutic or non-therapeutic breathing interfaces, such as full face masks, nasal masks, oral masks, and nasal pillows. Certain features, aspects and advantages of the method and apparatus of the present disclosure may be equally applied to other breathing devices for other conditions.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A nasal cannula, comprising:
    a cannula body defining a cavity;
    at least one curved, non-sealing nasal prong having a curved portion, the at least one curved, non-sealing nasal prong extending from the cannula, the at least one curved, non-sealing nasal prong having an interior passage in communication with the cavity, wherein the flow has a relatively low pressure on an inside curve of the interior passage and relatively high pressure on an outside curve of the interior passage, the flow prone to flow separation along the inside curve, the outside curve having a first length from the cannula body to a prong opening, the inside curve having a second length from the cannula body to the prong opening, the first length greater than the second length; and
    wherein the outside curve comprises a smooth inner surface defining the interior passage and the inside curve comprises a rough inner surface defining the interior passage, the rough inner surface formed by a plurality of turbulation elements provided on only the inside curve of the interior passage of the at least one curved, non-sealing nasal prong such that the outside curve of the interior passage of the at least one curved, non-sealing nasal prong omits a turbulation element, wherein the plurality of turbulation elements extend into a wall defining the inside curve, but not through the wall.

2. The nasal cannula of claim 1, wherein the plurality of turbulation elements is adapted to induce turbulence in a flow of breathing gas through the interior passage in a boundary layer at the inside curve.

3. The nasal cannula of claim 1, wherein the plurality of turbulation elements extends along the entire second length of the inside curve.

4. The nasal cannula of claim 1, wherein the plurality of turbulation elements extends along a portion of the second length of the inside curve.

5. The nasal cannula of claim 1, wherein a turbulation element of the plurality of turbulation elements extends along the inside curve in a circumferential direction.

6. The nasal cannula of claim 1, wherein an initial portion of the at least one curved, non-sealing nasal prong extending from a portion of the cannula body defining the cavity is generally straight.

7. The nasal cannula of claim 1, wherein the plurality of turbulation elements comprises random surface texturing.

8. The nasal cannula of claim 1, wherein features defining the plurality of turbulation elements are elongated along the inside curve in a circumferential direction.

9. The nasal cannula of claim 1, wherein a peak distance of a turbulation element of the plurality, of turbulation elements is more than 0% and less than 5% of a diameter of the at least one curved, non-sealing nasal prong.

10. The nasal cannula of claim 1, wherein the at least one curved, non-sealing nasal prong is formed as a unitary structure with the cannula body.

11. The nasal cannula of claim 1, wherein the at least one curved, non-sealing nasal prong is formed separately from a portion of the cannula body that defines the cavity.

12. A nasal cannula, comprising:
    a cannula body defining a cavity;
    at least one curved, non-sealing nasal prong having a curved portion, the at least one curved, non-sealing nasal prong extending from the cannula, the at least one curved, non-sealing nasal prong having an interior passage in communication with the cavity, an outside curve of the at least one curved non-sealing nasal prong having a first length from the cannula body to a prong opening, an inside curve of the at least one curved, non-sealing nasal prong having a second length from the cannula body to the prong opening, the first length greater than the second length; and wherein the inside curve comprises a smooth inner surface defining the interior passage and the outside curve comprises a rough inner surface defining the interior passage, the rough inner surface formed by a plurality of turbulation elements provided on only an outside curve of the interior passage of the at least one curved, non-sealing nasal prong such that an inside curve of the interior passage of the at least one curved, non-sealing nasal prong omits a turbulation element, wherein the plurality of turbulation elements extend into a wall defining the outside curve, but not through the wall, and, wherein the plurality of turbulation elements do not form an opening in the at least one curved, non-sealing nasal prong.

13. The nasal cannula of claim 12, wherein the plurality of turbulation elements present on the at least one curved, non-sealing nasal prong is configured to induce a laminar flow.

14. The nasal cannula of claim 1, wherein an inlet and an outlet of the at least one curved, non-sealing nasal prong are non-parallel or angled relative to one another.

15. The nasal cannula of claim 12, wherein the plurality of turbulation elements extends along the entire first length of the outside curve.

16. The nasal cannula of claim 12, wherein the plurality of turbulation elements extends along a portion of the first length of the outside curve.

* * * * *

UNITED STATES PATENT AND TRADEMARK OFFICE
CERTIFICATE OF CORRECTION

PATENT NO. : 10,933,210 B2  
APPLICATION NO. : 15/022451  
DATED : March 2, 2021  
INVENTOR(S) : Laurence Gulliver et al.

Page 1 of 1

It is certified that error appears in the above-identified patent and that said Letters Patent is hereby corrected as shown below:

In the Specification

In Column 4, Line 16 (approx.), delete "58," and insert --58.--.

In Column 5, Line 2, delete "onion" and insert --portion--.

In Column 5, Line 4, delete "onion" and insert --portion--.

In the Claims

In Column 6, Line 55, Claim 9, delete "plurality," and insert --plurality--.

In Column 7, Line 4, Claim 12, delete "curved" and insert --curved,--.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*